US010835207B2

(12) United States Patent
Altmann et al.

(10) Patent No.: US 10,835,207 B2
(45) Date of Patent: Nov. 17, 2020

(54) FAST ANATOMICAL MAPPING USING ULTRASOUND IMAGES

(75) Inventors: Andres Claudio Altmann, Haifa (IL); Nahum Kilim, Haifa (IL); Aviva Goldberg, Hadera (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1493 days.

(21) Appl. No.: 12/646,225

(22) Filed: Dec. 23, 2009

(65) Prior Publication Data

US 2011/0152684 A1 Jun. 23, 2011

(51) Int. Cl.
*A61B 8/00* (2006.01)
*G06T 17/00* (2006.01)
*A61B 8/12* (2006.01)
*A61B 8/08* (2006.01)
*G06T 7/593* (2017.01)

(52) U.S. Cl.
CPC .............. *A61B 8/4488* (2013.01); *A61B 8/12* (2013.01); *A61B 8/4254* (2013.01); *A61B 8/5238* (2013.01); *G06T 7/593* (2017.01); *G06T 17/00* (2013.01); *A61B 8/543* (2013.01); *G06T 2200/08* (2013.01); *G06T 2207/10132* (2013.01); *G06T 2207/30048* (2013.01)

(58) Field of Classification Search
USPC ........................................................ 600/443
See application file for complete search history.

(56) References Cited

U.S. PATENT DOCUMENTS

| 5,601,084 | A | 2/1997 | Sheehan et al. |
| 5,682,895 | A | 11/1997 | Ishiguro |
| 5,830,145 | A | 11/1998 | Tenhoff |
| 6,004,269 | A | 12/1999 | Crowley et al. |
| 6,266,551 | B1 | 7/2001 | Osadchy et al. |
| 6,443,894 | B1 | 9/2002 | Sumanaweera et al. |
| 6,690,963 | B2 | 2/2004 | Ben-Haim et al. |
| 6,716,166 | B2 | 4/2004 | Govari |

(Continued)

FOREIGN PATENT DOCUMENTS

| CN | 1853576 A | 11/2006 |
| CN | 1911471 A | 2/2007 |

(Continued)

OTHER PUBLICATIONS

Melton et al. ("Automatic real-time Endocardial edge detection in two-dimensional echocardiography"; ultrasonic imaging, 5, 300-307, 1983).*

(Continued)

*Primary Examiner* — Oommen Jacob
*Assistant Examiner* — Shahdeep Mohammed

(57) ABSTRACT

A method for three-dimensional (3D) mapping includes acquiring a plurality of two-dimensional (2D) ultrasonic images of a cavity in a body of a living subject, the 2D images having different, respective positions in a 3D reference frame. In each of the 2D ultrasonic images, pixels corresponding to locations within an interior of the cavity are identified. The identified pixels from the plurality of the 2D images are registered in the 3D reference frame so as to define a volume corresponding to the interior of the cavity. An outer surface of the volume is reconstructed, representing an interior surface of the cavity.

22 Claims, 3 Drawing Sheets

(56) References Cited

U.S. PATENT DOCUMENTS

| | | |
|---|---|---|
| 6,773,402 B2 | 8/2004 | Govari et al. |
| 6,968,299 B1 | 11/2005 | Bernardini et al. |
| 7,457,444 B2 | 11/2008 | Geiger et al. |
| 2002/0102023 A1 | 5/2002 | Yamauchi |
| 2002/0111553 A1* | 8/2002 | Brock-Fisher ......... A61B 8/481 600/443 |
| 2003/0153823 A1 | 8/2003 | Geiser et al. |
| 2005/0264578 A1* | 12/2005 | Engel ...................... G06T 15/04 345/582 |
| 2005/0283075 A1* | 12/2005 | Ma et al. ....................... 600/441 |
| 2006/0072802 A1* | 4/2006 | Higgs et al. ................. 382/131 |
| 2006/0241445 A1* | 10/2006 | Altmann et al. .............. 600/443 |
| 2007/0043296 A1 | 2/2007 | Schwartz |
| 2008/0123923 A1* | 5/2008 | Gielen ................. G06K 9/3216 382/131 |
| 2008/0137927 A1 | 6/2008 | Altmann et al. |
| 2010/0099991 A1 | 4/2010 | Snyder |
| 2010/0215238 A1* | 8/2010 | Lu ............................ G06T 7/12 382/131 |

FOREIGN PATENT DOCUMENTS

| | | |
|---|---|---|
| CN | 101404940 A | 4/2009 |
| CN | 101548897 A | 10/2009 |
| EP | 1750216 A1 | 2/2007 |
| EP | 1929956 A2 | 6/2008 |
| JP | 2002-224116 A | 8/2002 |
| JP | 2006-305361 A1 | 11/2006 |
| JP | 2009-011581 A | 1/2009 |
| JP | 2009-136679 A | 6/2009 |
| WO | WO 99/55233 A1 | 11/1999 |
| WO | WO 00/19908 A1 | 4/2000 |
| WO | WO 2005030057 A1 | 4/2005 |
| WO | WO 2005112773 A2 | 12/2005 |
| WO | WO 2007107926 A1 | 9/2007 |

OTHER PUBLICATIONS

Engel et al. (semiautomatic determination of the reconstruction volume for real-time freehand 3D ultrasound reconstruction; SPIE Medical Imaging, 2009).*

Specht A R et al. Surface segmentation using a modified ball-pivoting algorithm, Image Processing, 2004. ICIP 04. 2004 Int'l Conf on Singapore, vol. 3, Oct. 24, 2004; pp. 1931-1934, XP01078645 ISBN 978-0-7803-8554-2.

European Office Action dated Dec. 4, 2012 received in related EP 06 252 210.7-2319.

Extended European Search Report dated Apr. 19, 2011 received in related EP 10252188.7-2319.

English language translation of Japanese Office Action dated Feb. 3, 2015 received in related JP 2010-285661.

English language translation of Japanese Office Action dated May 27, 2014 received in related JP 2010-285661.

Australian Office Action dated Jun. 12, 2014 received in related AU 2010257203.

Chinese Office Action dated Mar. 23, 2015 from related Chinese Application No. 201010620927.7, together with an English language translation.

AU2010257203 Examination Report dated Jul. 6, 2015.

EP10252188.7 Examination Report dated Nov. 11, 2015.

CN201010620927.7 Search Report dated Mar. 20, 2014.

CA 2,726,390 Office Action dated Oct. 25, 2016.

Canadian Search Report, Application No. 2,726,390 dated Apr. 10, 2017.

Dai, Y. et al., "Semiautomatic determination of the reconstruction volume for real-time freehand 3D ultrasound reconstruction", Proceedings of SPIE, The International Society for Optical Engineering, Feb. 2009.

Canadian office action for corresponding patent application No. 2,726,390, dated Dec. 18, 2019.

* cited by examiner

FAST ANATOMICAL MAPPING USING ULTRASOUND IMAGES

FIELD OF THE INVENTION

The present invention relates generally to ultrasound imaging, and specifically to methods and systems for three-dimensional (3D) reconstruction of anatomical structures based on ultrasound images.

BACKGROUND OF THE INVENTION

A variety of devices and methods for intracardiac ultrasonic imaging are known in the art. For example, Biosense Webster Inc. (Diamond Bar, Calif.) offers the CartoSound™ system and SoundStar™ catheter for producing 3D ultrasound images in real time. The SoundStar catheter, which is inserted through the vascular system into the heart, contains a position sensor and a phased array of ultrasound transducers. The CartoSound system processes the signals from the position sensor and the ultrasound transducers to generate 3D images of the heart chambers.

Several methods are known in the art for non-contact reconstruction of the endocardial surface using intracardial ultrasonic imaging. For example, PCT International Publication WO 00/19908, whose disclosure is incorporated herein by reference, describes a steerable transducer array for intracardial ultrasonic imaging. The array forms an ultrasonic beam, which is steered in a desired direction by an active aperture. U.S. Pat. No. 6,004,269, whose disclosure is also incorporated herein by reference, describes an acoustic imaging system based on an ultrasound device that is incorporated into a catheter. The ultrasound device directs ultrasonic signals toward an internal structure in the heart to create an ultrasonic image.

As another example, PCT International Publication WO 99/55233, whose disclosure is incorporated herein by reference, describes a method for delineating a 3-D surface of a patient's heart. A 3-D mesh model is developed using training data, to serve as an archetypal shape for a population of patient hearts. Multiple ultrasound images of the patient's heart are taken in different image planes. Anatomical locations are manually identified in each of the images. The mesh model is rigidly aligned with the images in respect to the predefined anatomical locations.

This sort of manual assistance in delineating contours is common in methods for 3D reconstruction based on ultrasound images. For example, U.S. Patent Application Publication 2006/0241445, whose disclosure is incorporated herein by reference, describes a method for modeling of an anatomical structure, in which a plurality of ultrasonic images of the anatomical structure are acquired using an ultrasonic sensor, at a respective plurality of spatial positions of the ultrasonic sensor. Location and orientation coordinates of the ultrasonic sensor are measured at each of the plurality of spatial positions. Contours-of-interest that refer to features of the anatomical structure are marked in one or more of the ultrasonic images. A three-dimensional (3D) model of the anatomical structure is constructed, based on the contours-of-interest and on the measured location and orientation coordinates.

SUMMARY

Embodiments of the present invention that are described hereinbelow provide fast, accurate methods for reconstructing 3D surfaces from collections of 2D ultrasound images.

There is therefore provided, in accordance with an embodiment of the present invention, a method for three-dimensional (3D) mapping, including acquiring a plurality of two-dimensional (2D) ultrasonic images of a cavity in a body of a living subject, the 2D images having different, respective positions in a 3D reference frame. In each of the 2D ultrasonic images, pixels corresponding to locations within an interior of the cavity are identified. The identified pixels from the plurality of the 2D images are registered in the 3D reference frame so as to define a volume corresponding to the interior of the cavity. A processor reconstructs an outer surface of the volume, which represents an interior surface of the cavity.

In some embodiments, acquiring the plurality of the 2D images includes inserting a probe including an ultrasound imaging device into the body, and capturing the 2D images using the probe inside the body. In a disclosed embodiment, inserting the probe includes inserting a catheter into a heart of the subject, and wherein the volume corresponds to the interior of a chamber of the heart. Inserting the catheter typically includes positioning the catheter so that the ultrasound imaging device is in a first chamber of the heart, wherein the volume may correspond to the interior of a second chamber of the heart, other than the first chamber, such that reconstructing the outer surface includes generating a 3D map of the interior surface of the second chamber.

Typically, acquiring the plurality of the 2D images includes capturing the 2D images using an ultrasound probe including a position transducer, and registering the identified pixels includes receiving and processing signals associated with the position transducer so as to find coordinates of the probe in the 3D reference frame, and registering the identified pixels in the 3D reference frame using the coordinates.

In some embodiments, identifying the pixels in the 2D ultrasonic images includes classifying pixels corresponding to locations in the body having a low reflectance as belonging to the interior of the cavity. Typically, classifying the pixels includes setting a threshold value, and classifying the pixels having respective gray-scale values below a specified threshold as belonging to the interior of the cavity. In alternative embodiments, acquiring the two-dimensional (2D) ultrasonic images includes capturing Doppler images in which color represents flow, and wherein identifying the pixels includes classifying pixels as belonging to the interior of the cavity responsively to respective color values of the pixels.

In a disclosed embodiment, reconstructing the outer surface includes applying a ball-pivoting algorithm to the pixels in the volume. Applying the ball-pivoting algorithm may include processing the pixels with a resolution of reconstruction that varies over the volume.

There is also provided, in accordance with an embodiment of the present invention, apparatus for three-dimensional (3D) mapping, including an ultrasound probe, which is configured to capture a plurality of two-dimensional (2D) ultrasonic images of a cavity in a body of a living subject, the 2D images having different, respective positions in a 3D reference frame. A processor is configured to identify in each of the 2D ultrasonic images pixels corresponding to locations within an interior of the cavity, to register the identified pixels from the plurality of the 2D images in the 3D reference frame so as to define a volume corresponding to the interior of the cavity, and to reconstruct an outer surface of the volume, which represents an interior surface of the cavity.

There is additionally provided, in accordance with an embodiment of the present invention, a computer software product, including a computer-readable medium in which program instructions are stored, which instructions, when read by a processor, cause the processor to receive a plurality of two-dimensional (2D) ultrasonic images of a cavity in a body of a living subject, the 2D images having different, respective positions in a 3D reference frame, to identify in each of the 2D ultrasonic images pixels corresponding to locations within an interior of the cavity, to register the identified pixels from the plurality of the 2D images in the 3D reference frame so as to define a volume corresponding to the interior of the cavity, and to reconstruct an outer surface of the volume, which represents an interior surface of the cavity.

The present invention will be more fully understood from the following detailed description of the embodiments thereof, taken together with the drawings in which:

DETAILED DESCRIPTION OF EMBODIMENTS

Figure 1:
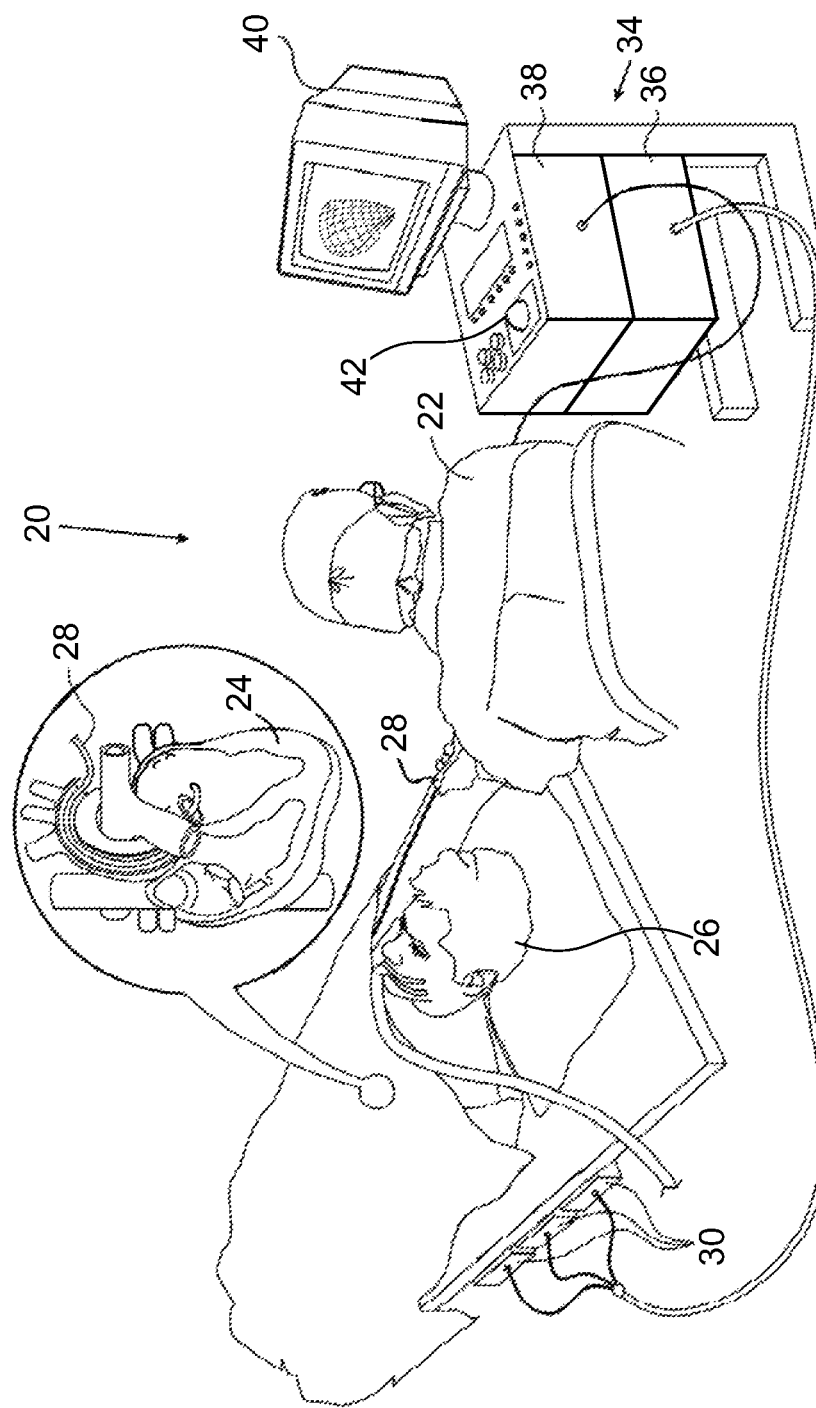
FIG. 1 is a schematic, pictorial illustration of a catheter-based system for ultrasonic imaging, in accordance with an embodiment of the present invention.
Figure 2:
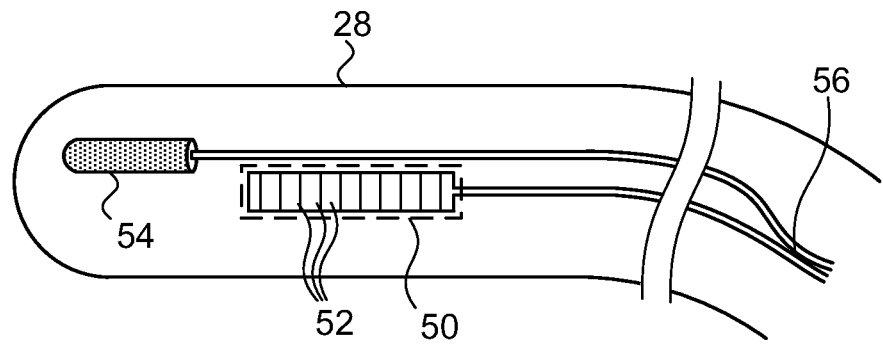
FIG. 2 is a schematic side view of the distal end of a catheter used in the system of FIG. 1.

Reference is now made to FIGS. 1 and 2, which schematically illustrate a catheter-based ultrasound imaging system 20, in accordance with an embodiment of the present invention. FIG. 1 is a pictorial illustration of the overall system, while FIG. 2 is a side view of the distal end of a probe, such as a catheter 28, that is used in the system. This system and catheter are shown here by way of illustration, to assist in understanding the methods of ultrasound-based 3D mapping that are described further below. These methods, however, are not limited to catheter-based ultrasonic sensing and may similarly be applied, mutatis mutandis, using 2D or 3D ultrasound images acquired by other types of probes, both intra- and extra-corporeal. Furthermore, these methods may be used in mapping of other anatomical cavities, not only in the heart.

As shown in FIG. 1, an operator 22, such as a physician, inserts catheter 28 into the body of a patient 26, so that the distal end of the catheter passes through the vascular system into the patient's heart 24. The catheter is connected at its proximal end to a console 34, which typically comprises a processor 38 with suitable signal processing and user interface circuits. This processor receives and processes signals from catheter 28, as described hereinbelow. Processor 38 may comprise a general-purpose computer processor, which is programmed in software to carry out the functions that are described herein. This software may be downloaded to the processor in electronic form, over a network, for example. Alternatively or additionally, the software may be stored on tangible computer-readable storage media, such as optical, magnetic, or electronic memory media. Further additionally or alternatively, at least some of the functions of the processor may be carried out by a digital signal processor (DSP) or by dedicated or programmable hardware logic circuits.

Typically, console 34 also enables a user to observe and regulate the functions of catheter 28 and to view and edit images that are formed using the catheter. For these purposes, the console comprises a display 40 and a user interface 42.

As shown in FIG. 2, the distal end of catheter 28 comprises an ultrasound imaging device 50, which is used to produce ultrasound images of the inside of the body. Device 50 typically comprises a phased array of transducers 52, which is operated, as is known in the art, so as to capture a two-dimensional (2D) "fan" image in the plane of the scanning ultrasonic beam (referred to herein as the "beam plane" or "image plane"), which contains the longitudinal axis of the catheter. The transducers receive ultrasonic waves that are reflected from objects in the beam plane and output signals in response to the reflected waves. Typically, these signals are conveyed by wires 56 running through catheter 28 to console 34, which processes the signals in order to form and display ultrasound images and 3D maps, as described hereinbelow.

The distal end of catheter 28 further comprises a position sensor 54, which generates signals that indicate the position (location and orientation) of the catheter within the body. Based on these position signals, console 34 determines the location and orientation of each fan image captured by imaging device 50. Processor 38 is thus able to determine the coordinates of objects appearing in the fan image, as well as to register and combine multiple 2D images captured at different catheter positions.

In the pictured embodiment, system 20 uses magnetic position sensing to determine position coordinates of the distal end of catheter 28 inside heart 24. To determine the position coordinates, a driver circuit 36 in console 34 drives field generators 30 to generate magnetic fields within the body of patient 26. Typically, field generators 30 comprise coils, which are placed below the patient's torso at known positions external to the body. These coils generate magnetic fields in a predefined working volume that contains heart 24. Sensor 54, which may comprise, for example, one or more coils within the distal end of catheter 28, generates electrical signals in response to these magnetic fields. Processor 38 processes these signals in order to determine the position (location and orientation) coordinates of the distal end of catheter 28. Console 34 may use the coordinates in driving display 40 to show the location and status of the catheter.

This method of position sensing and processing is implemented in the CARTO™ system produced by Biosense Webster Inc. This sort of magnetic position sensing is described in detail, for example, in U.S. Pat. No. 6,266,551, whose disclosure is incorporated herein by reference. Other systems that combine ultrasonic imaging with magnetic position sensing are described in U.S. Pat. Nos. 6,690,963, 6,716,166 and 6,773,402, whose disclosures are also incorporated herein by reference.

Alternatively or additionally, system 20 may comprise an automated mechanism (not shown) for maneuvering and operating catheter 28 within the body of patient 26. In such embodiments, processor 38 generates a control input for controlling the motion of the catheter based on the signals provided by the position sensing system.

Although FIG. 1 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter 28 that causes console 34 to receive signals indicative of the coordinates of the element. The position transducer may thus comprise a receiver in the catheter, such as sensor 54, which generates a position signal to the control unit based on energy received by the transducer; or it may comprise a transmitter, emitting energy that is sensed by a receiver external to the probe. Furthermore, the methods described hereinbelow may similarly be applied in mapping and imaging applications using not only catheters, but also probes of other types, both in the heart and in other body organs and regions, as well as ultrasound probes external to the body.

Figure 3:
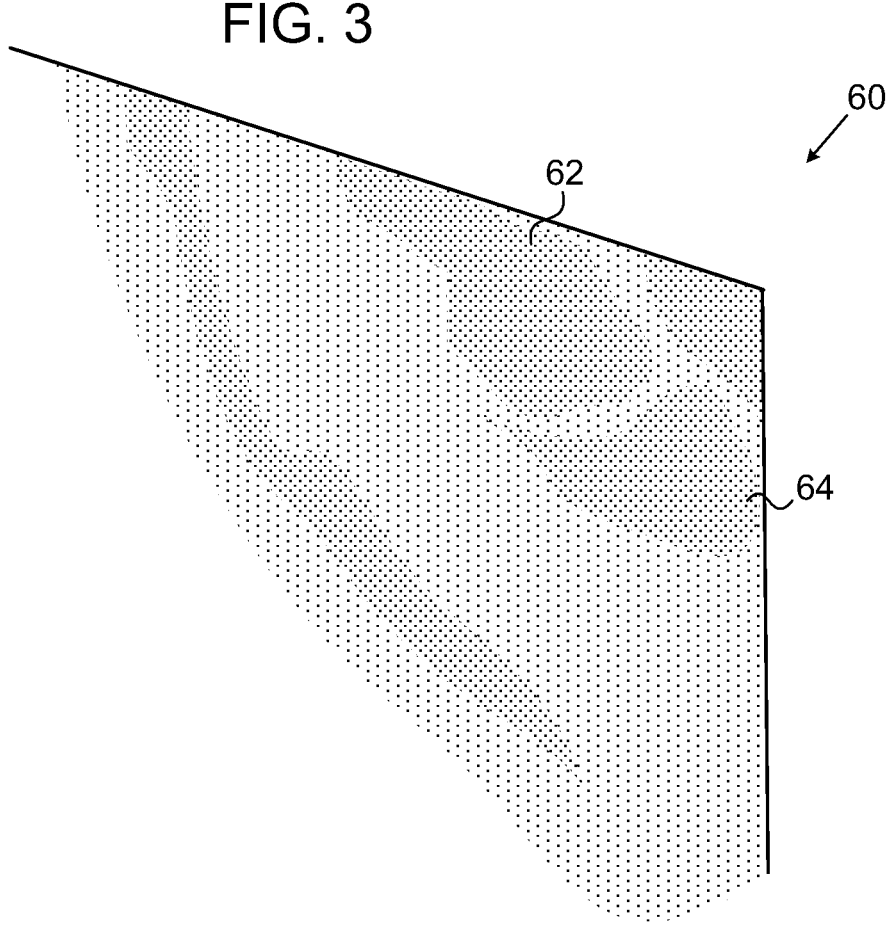
FIG. 3 is a schematic representation of an ultrasound image captured by a catheter, in accordance with an embodiment of the present invention.

FIG. 3 is a schematic representation of an ultrasound image 60 captured by catheter 28, in accordance with an embodiment of the present invention. The image has the form of a 2D fan, with its vertex at imaging device 50. As noted above, console 34 can determine the location of the vertex and the orientation of the fan in 3D space based on the signals received from position sensor 54. Dark areas 62, 64 in the image correspond to areas, such as the heart chambers, that are filled with blood and therefore have low reflectance. Brighter areas generally represent tissue, such as the internal and external heart walls.

As noted earlier, operator 22 may manipulate catheter 28 inside heart 24 to capture images from different locations and at different orientations. The reflections that make up the images may originate not only from the heart chamber in which the distal end of the catheter is located, but also from other heart chambers and anatomical structures. Thus, for example, catheter 28 may be inserted into the right atrium (which is relatively easy to access via the vena cava) and may capture images from the right atrium of the left atrium and possibly the ventricles.

Figure 4:
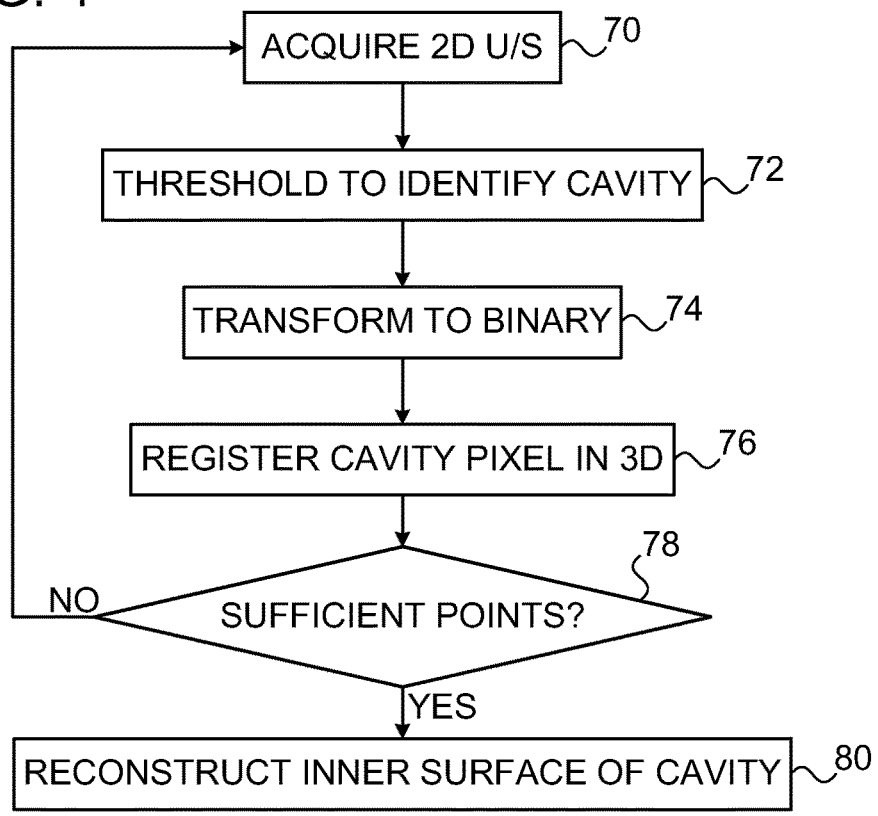
FIG. 4 is a flow chart that schematically illustrates a method for fast anatomical mapping using ultrasound images, in accordance with an embodiment of the present invention.

FIG. 4 is a flow chart that schematically illustrates a method for fast anatomical mapping using ultrasound images, in accordance with an embodiment of the present invention. At each iteration of the method, sensor 50 acquires a 2D ultrasound fan image, having the general form of image 60 (FIG. 3), at an image acquisition step 70. Image acquisition may be gated to a certain annotation point in the heart cycle (such as systole or diastole), using an electro-cardiogram (ECG) monitor for synchronization, for example, or the images may alternatively be acquired continuously, without gating. Processor 38 identifies the inside of the heart chamber of interest (the blood pool area) in each 2D image acquired by the ultrasound catheter, at a cavity identification step 72. These "dark," low-reflectance areas may be identified, for example, by applying a threshold to the gray scale levels of the ultrasound image. The threshold may be set automatically or manually. Any suitable method known in the art may be used to choose the threshold automatically, such as the Otsu method, in which the threshold is chosen based on clustering of the pixel gray-scale values.

Alternatively, other ultrasound imaging modes may be used in image capture at step 70, and the method used to identify the cavity at step 72 may be adapted accordingly. For example, the 2D images may be acquired using Doppler imaging techniques, such as Color Doppler, Power Doppler or Tissue Imaging Doppler, as are known in the art. Such techniques use image color (commonly referred to as pseudo-color) to represent flow. In Color Doppler, areas of blood flow are colored in the image, while areas of tissue are not. In this case, pixels having a color value above a certain threshold may be identified as belonging to the blood pool area at step 72. On the other hand, in Tissue Imaging Doppler, areas of tissue are colored while blood is not, so that pixels having a color value below a certain threshold will be identified as belonging to the blood pool area.

Whichever imaging modality is used, processor 38 applied the threshold to transform the 2D gray-scale or color image into a binary image, at a binarization step 74. In the binary image, pixels with the value '0' are classified as belonging to areas of blood, while pixels with the value '1' belong to tissue. Other image processing operations may be applied in order to improve the precision of separation between blood and tissue separation. For example, morphological erosion and dilation may be applied in succession to remove small dark areas, which may have been misidentified as blood pool areas, within tissue regions.

Processor 38 finds the vertex location and the orientation of the captured 2D image, at an image registration step 76. As noted above, the processor computes the location and orientation coordinates on the basis of the signals output by position sensor 54. Given the vertex position and image orientation, the processor can calculate the 3D coordinates of every pixel in the binarized image in the fixed 3D reference frame of field generators 30, and thus registers the 2D image pixels in the 3D volume.

After capturing each 2D image, the operator moves the catheter tip in the heart, and the above 2D image capture and processing steps are repeated until the processor has collected a sufficient number of binary pixel values within the volume of interest, at a capture completion step 78.

Processor 38 collects the pixels with value '0' (blood) and finds the outer surface bounding these pixels, at a surface reconstruction step 80. The outer surface bounding the blood pool in a heart chamber is the inner surface of the heart wall surrounding that chamber. Thus, by finding the bounding outer surface of the blood pool the processor has, in effect, constructed a 3D map of the chamber in question. Optionally, the processor may continue acquiring 2D images while reconstructing the 3D surface and may thus refine the map progressively.

Using the blood pool in the 3D domain as the basis for surface reconstruction has the advantage of offering a fast, efficient way to overcome the problem of image segmentation. Various algorithms may be used to reconstruct the outer surface of a volume based on a collection of interior points of this sort. For example, processor 38 may apply the ball-pivoting algorithm that is described in U.S. Pat. No. 6,968,299, whose disclosure is incorporated herein by reference. This algorithm computes a triangle mesh interpolating a given point cloud by "rolling" a ball of a certain radius over the point cloud. The vertices of the triangles that are found in this way define the outer surface of the cloud.

To reduce the computational load, not all the '0' pixels are necessarily used in building the model, and processor 38 may apply different resolution levels in different areas. The above-mentioned ball-pivoting algorithm may be adapted for this sort of variable-resolution mapping by using different ball radii in different regions of the map. High resolution is typically needed only in the blood-tissue interface area (along the edge of the blood pool). This area can be identified automatically or manually in the binary images. The processor then performs high-resolution reconstruction only near the tissue boundary, and uses low resolution elsewhere. In other words, the processor uses fewer pixels from the 2D images in areas far from the tissue, and more pixels in the area of the tissue interface (typically within a thickness on the order of 1 mm).

After processor 38 has reconstructed and displayed the 3D map in the manner described above, a user may apply image editing tools, via user interface 42, for example, to cut and/or morph the model in order to correct artifacts and remove features that are not of interest.

Figure 5:
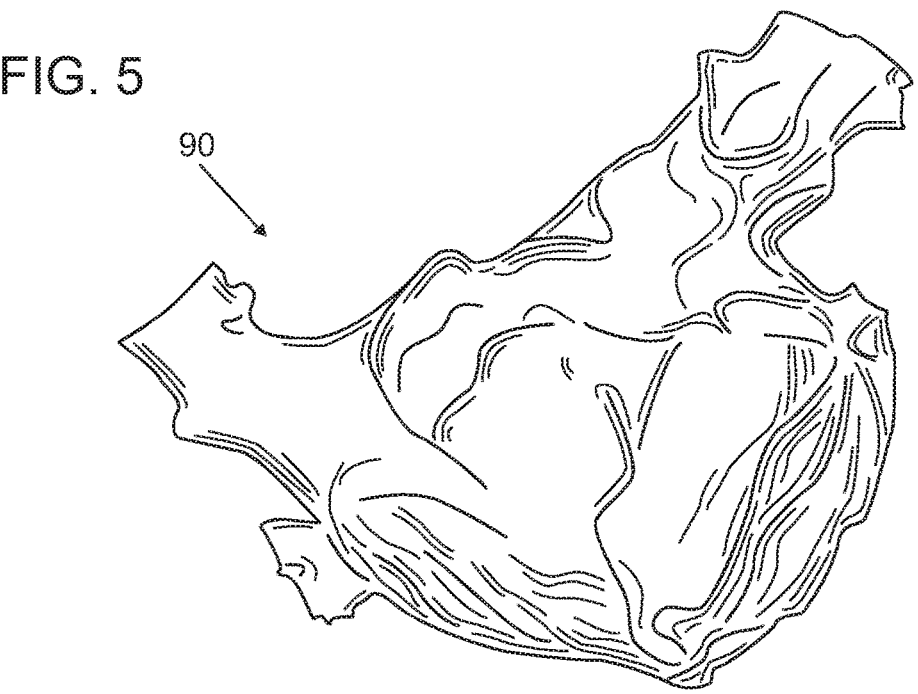
FIG. 5 is a schematic representation of a 3D map of a heart chamber produced in accordance with an embodiment of the present invention.

FIG. 5 is a schematic representation of a 3D map 90 of a heart chamber, of a type that may be produced by the above method in accordance with an embodiment of the present invention. The map in this case shows the left ventricle of the heart, including parts of the pulmonary veins. This sort of map may be used for various purposes, such as serving as a starting point for an electro-anatomical map (of the type produced by the above-mentioned CARTO system) or for segmentation of a full 3D ultrasonic or tomographic image.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for three-dimensional (3D) mapping of a cavity having an inner surface and including a blood pool area in a body of a living subject, comprising: providing a computer processor programmed to perform at least one algorithm disclosed herein, for determining, in a 3D domain, an outer surface of the blood pool area which represents the inner surface of the cavity wherein the at least one algorithm comprises the steps of:
   (i) acquiring a plurality of 2D ultrasonic images including the cavity in the body of the living subject, the 2D images having different, respective positions in a 3D reference frame;
   (ii) applying a threshold to gray scale levels of the 2D ultrasound images wherein the threshold is set to identify pixels that have low reflectance and correspond to blood pool area pixels;
   (iii) identifying in each of the 2D ultrasonic images, blood pool area pixels corresponding to locations within an interior of the cavity based on the low reflectance of said blood pool area pixels;
   (iv) determining a vertex and an orientation for each of the plurality of 2D ultrasonic images based on signals output by a position transducer in an ultrasound probe to calculate 3D coordinates of the 3D reference frame of every pixel;
   (v) registering all of the identified blood area pixels from the plurality of the 2D images in the 3D reference frame so as to define a volume of the blood pool area pixels by converting coordinates of the identified blood pool area pixels from 2D coordinates having low reflectance into 3D coordinates of the 3D reference frame;
   (vi) reconstructing, in the 3D domain, the outer surface of the volume of the blood pool areal pixels which represents the inner surface of the cavity; and
   (v) wherein reconstructing the outer surface comprises processing the blood pool area pixels with a resolution of reconstruction that varies over the volume, where a higher resolution is used for pixels proximate to a tissue boundary and a lower resolution is used for pixels not proximate to a tissue boundary.

2. The method according to claim 1, wherein acquiring the 2D ultrasonic images comprises capturing Doppler images in which color represents flow, and wherein identifying the blood pool area pixels comprises classifying blood pool area pixels as belonging to the interior of the cavity responsively to respective color values of the blood pool area pixels.

3. The method according to claim 1, wherein reconstructing the outer surface comprises applying a ball-pivoting algorithm to the blood pool area pixels in the volume.

4. The method according to claim 1, including the step of applying the threshold to transform the 2D gray scale image into a binary image.

5. The method according to claim 1, wherein acquiring the plurality of the 2D images comprises inserting the ultrasound probe comprising an ultrasound imaging device into the body, and capturing the 2D images using the probe inside the body.

6. The method according to claim 5, wherein the cavity is a heart and wherein inserting the probe comprises inserting a catheter into the heart of the subject, and wherein the cavity corresponds to the interior of a chamber of the heart.

7. The method according to claim 6, wherein inserting the catheter comprises positioning the catheter so that the ultrasound imaging device is in a first chamber of the heart, and wherein the cavity corresponds to the interior of a second chamber of the heart, other than the first chamber, such that reconstructing the outer surface comprises generating a 3D map of the interior surface of the second chamber.

8. The method according to claim 1, wherein classifying the blood pool area pixels comprises setting the threshold value, and classifying the blood pool area pixels having respective gray-scale values below the threshold value as belonging to the interior of the cavity.

9. The method according to claim 8, wherein the threshold value is automatically determined based on clustering of pixel values.

10. Apparatus for three-dimensional (3D) mapping of a cavity having an inner surface and including a blood pool area in a body of a living subject, comprising:
   an ultrasound probe, which is configured to determine an outer surface of the blood pool area which represents the inner surface of the cavity by acquiring a plurality of 2D ultrasonic images including the cavity in the body of living subject, the 2D images having different, respective positions in a 3D reference frame, the ultrasound probe comprises a position transducer; and
   a computer processor programmed to perform at least one algorithm disclosed herein, for determining, in a 3D domain, the outer surface of the blood pool area which represents the inner surface of the cavity, wherein the at least one algorithm comprises the steps of (i) acquiring a plurality of the 2D ultrasonic images including the cavity in the body of a living subject, the 2D ultrasonic images having different, respective positions in the 3D reference frame, (ii) applying a threshold, to gray scale levels of the 2D ultrasound images wherein the threshold is set to identify pixels that have low reflectance and correspond to blood pool area pixels; (iii) identifying in each of the 2D ultrasonic images, blood pool area pixels corresponding to locations within an interior of the cavity based on the low reflectance of said blood pool area pixels and an adjustable threshold value for said blood pool area pixels (iv) determining a vertex and an orientation for each of the plurality of 2D ultrasonic images based on signals output by a position transducer in the ultrasound probe to calculate 3D coordinates of the 3D reference frame of every pixel, (v) registering all of the identified blood area pixels from the plurality of the 2D images in the 3D reference frame so as to define a volume of the blood pool area pixels by converting coordinates of the identified blood pool area pixels from 2D coordinates having low reflectance into 3D coordinates of the 3D reference frame, (vi) reconstructing, in the 3D domain, the outer surface of the volume of the blood pool area pixels which represents the inner surface of the cavity; and (v) wherein reconstructing the outer surface comprises processing the blood pool area pixels with a resolution of reconstruction that varies over the volume, where a higher resolution is used for pixels proximate to a tissue boundary and a lower resolution is used for pixels not proximate to a tissue boundary.

11. The apparatus according to claim 10, wherein the at least one algorithm of the computer processor is configured to set the threshold value, and to classify the blood pool area pixels having respective gray-scale values below the threshold value as belonging to the interior of the cavity.

12. The apparatus according to claim 10, wherein the 2D ultrasonic images comprise Doppler images in which color represents flow, and wherein the at least one algorithm of the computer processor is configured to classify blood pool area pixels as belonging to the interior of the cavity responsively to respective color values of the blood pool area pixels.

13. The apparatus according to claim 10, wherein the at least one algorithm of the computer processor is configured to apply a ball-pivoting algorithm to the blood pool area pixels in the volume in order to reconstruct the outer surface of the volume.

14. The apparatus according to claim 10, wherein the at least one algorithm includes the step of applying the threshold to transform the 2D gray scale image into a binary image.

15. The apparatus according to claim 10, wherein the ultrasound probe is configured to be inserted into the body and to capture the 2D images inside the body.

16. The apparatus according to claim 15, wherein the cavity is a heart and the probe comprises a catheter for insertion into the heart of the subject, wherein the catheter comprises an ultrasound imaging device, and wherein the volume corresponds to the interior of a chamber of the heart.

17. The apparatus according to claim 16, wherein the catheter is configured to be inserted into the heart so that the ultrasound imaging device is in a first chamber of the heart, and
wherein the cavity corresponds to the interior of a second chamber of the heart, other than the first chamber, such that reconstructing the outer surface comprises generating a 3D map of the interior surface of the second chamber.

18. A computer software product, comprising a non-transitory computer-readable medium in which program instructions are stored, which instructions, when read by a computer processor programmed to perform at least one algorithm disclosed herein for determining, in a 3D domain, outer surface of the blood pool area which represents an inner surface of the cavity, wherein the at least one algorithm comprises the steps of (i) acquiring a plurality of 2D ultrasonic images including a cavity in a body of living subject, the 2D images having different, respective positions in a 3D reference frame, (ii) applying a threshold, to gray scale level of the 2D ultrasound images wherein the threshold is set to identify pixels that have low reflectance and correspond to blood pool area pixels; (iii) identifying in each of the 2D ultrasonic images, blood pool area pixels corresponding to locations within an interior of the cavity based on the low reflectance of said blood pool area pixels and an adjustable threshold value for said blood pool area pixels (iv) determining a vertex and an orientation for each of the plurality of 2D ultrasonic images based on signals output by a position transducer in an ultrasound probe to calculate 3D coordinates of the 3D reference frame of every pixel, and (v) registering all of the identified blood area pixels from the plurality of the 2D images in the 3D reference frame so as to define a volume of the blood pool area pixels by converting coordinates of the identified blood pool area pixels from 2D coordinates having low reflectance into 3D coordinates of the 3D reference frame using the determined vertex and the orientation for each of the plurality of 2D ultrasonic images and registering the identified blood pool area pixels in the 3D reference frame, (vi) reconstructing, in the 3D domain, the outer surface of the volume of the blood pool area pixels which represents the inner surface of the cavity; and (v) wherein reconstructing the outer surface comprises processing the blood pool area pixels with a resolution of reconstruction that varies over the volume, where a higher resolution is used for pixels proximate to a tissue boundary and a lower resolution is used for pixels not proximate to a tissue boundary.

19. The product according to claim 18, wherein the instructions cause the processor to apply a ball-pivoting algorithm to the pixels in the volume in order to reconstruct the outer surface.

20. The computer software product according to claim 18 wherein the at least one algorithm includes the step of applying the threshold to transform the 2D gray scale image into a binary image.

21. The product according to claim 18, wherein the cavity is a heart and the volume corresponds to the interior of a chamber of the heart.

22. The product according to claim 21, wherein the 2D ultrasonic images are captured using an ultrasound imaging device in a first chamber of the heart, and wherein the cavity corresponds to the interior of a second chamber of the heart, other than the first chamber, such that reconstructing the outer surface comprises generating a 3D map of the interior surface of the second chamber.

* * * * *